US00PP37103P2

(12) United States Plant Patent
Grazzini

(10) Patent No.: US PP37,103 P2
(45) Date of Patent: Nov. 18, 2025

(54) **GARDEN CULINARY *SALVIA* PLANT NAMED 'G22088'**

(50) Latin Name: *Salvia officianalis*
Varietal Denomination: G22088

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 19/025,361

(22) Filed: Jan. 16, 2025

(51) Int. Cl.
*A01H 6/50* (2018.01)
*A01H 5/02* (2018.01)

(52) U.S. Cl.
USPC ..... Plt./475

(58) Field of Classification Search
USPC ..... Plt./475
CPC ..... A01H 6/508; A01H 5/02
See application file for complete search history.

*Primary Examiner* — Keith O. Robinson

(57) ABSTRACT

A new and distinct cultivar of *Salvia* plant named 'G22088' is disclosed, characterized by large, thick, rugose foliage. Plants have been observed to tolerate leaf pathogens(specifically powdery mildew). Both flowers and foliage are large. Leaves are intensely flavored and fragrant. The new variety is a *Salvia*, normally used for outdoor ornamental and culinary purposes.

2 Drawing Sheets

Figure 1:
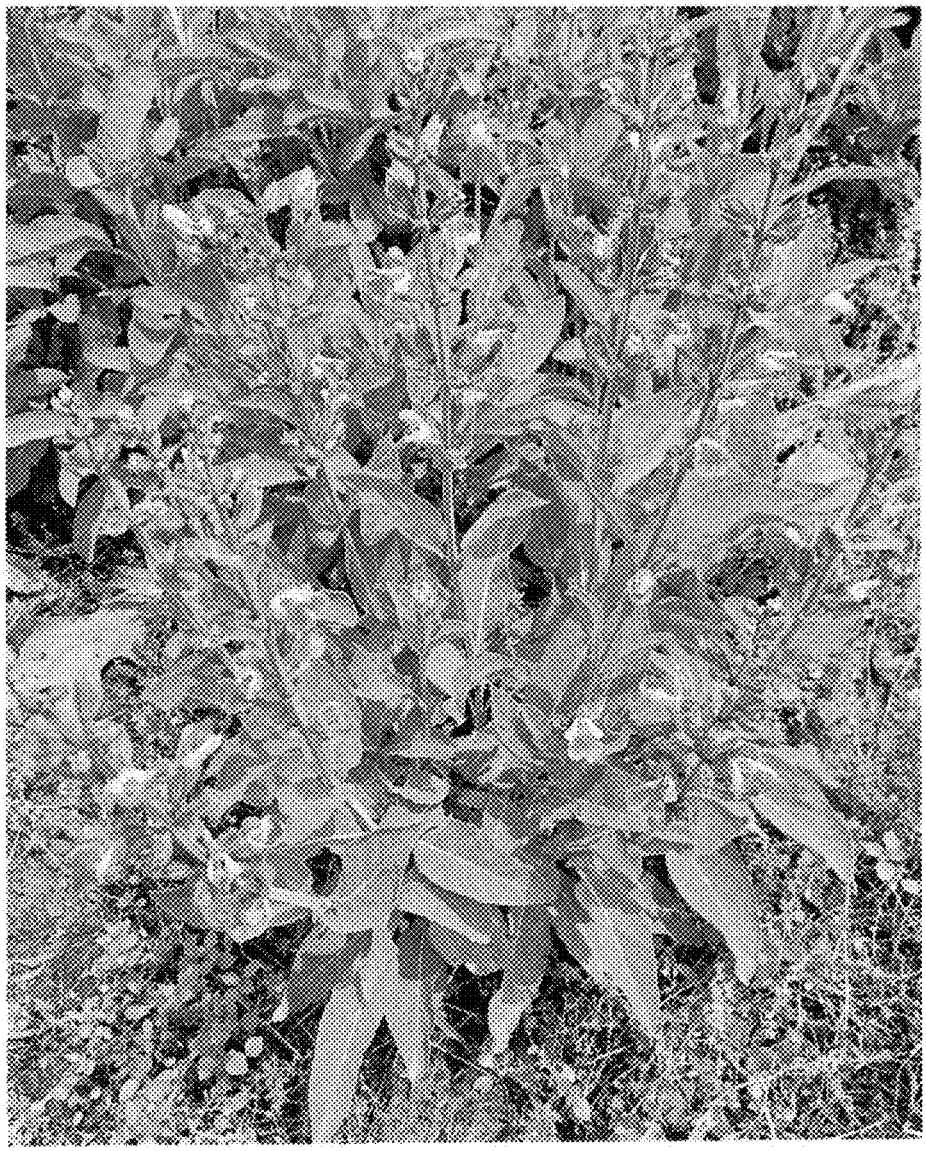

Latin name of the genus and species: *Salvia officianalis*. Variety denomination: 'G22088'.

BACKGROUND OF THE INVENTION

The new Salvia cultivar is a product of a planned breeding program conducted by the inventor at a research nursery in Bellefonte, Pennsylvania. The self-pollination resulting in this new variety was made during 2018.

The parent is the unpatented proprietary variety referred to as *Salvia* 'G12-338'. The new variety was selected in August of 2019 by the inventor in a group of seedlings resulting from the self-pollination, in a nursery in Bellefonte, Pennsylvania.

Asexual reproduction of the new cultivar was performed by vegetative cuttings, at the same nursery in Bellefonte, Pennsylvania during August of 2019, and has shown that the unique features of this cultivar are stable and reproduced true to type in multiple successive generations.

SUMMARY OF THE INVENTION

The cultivar 'G22088' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G22088'. These characteristics in combination distinguish 'G22088' as a new and distinct *Salvia* cultivar:

1. Thicker, more rugose foliage than typical of culinary garden sage.
2. Large foliage, larger than typical for culinary garden sage
3. More intense flavor and fragrance than typical of culinary garden sage.

4. Large blue-violet flowers, larger than typical of culinary garden sage.
5. Observed more tolerant of foliar plant pathogens (powdery mildew) than common culinary garden sage.

PARENT COMPARISON

Plants of the new cultivar 'G22088' are similar to plants of the parent in most horticultural characteristics; however, plants of the new cultivar 'G22088' differ in the following:

1. 'G22088' is more uniform in leaf size than parent 'G12-338'.
2. The foliage of 'G22088'is more glaucous grey-green foliage than parent 'G12-338'.
3. 'G22088' has a higher rooting efficiency (roots more readily) than 'G12-338'.
4. 'G22088' is more intensely flavored than 'G12-338'.
5. 'G22088' produces fewer seeds than 'G12-338' when self-pollinated.

COMMERCIAL COMPARISONS

Plants of the new cultivar 'G22088' are comparable to the commercial variety *Salvia* 'Berggarten', unpatented. The two *Salvia* varieties are similar in most horticultural characteristics, however, the new variety 'G22088' differs in the following:

1. 'G22088' has larger and thicker leaves than 'Berggarten'.
2. Leaves of 'G22088' leaves less grey-green than leaves of comparator 'Berggarten'.
3. Leaves of 'G22088' are more intensely fragrant and flavorful than those of 'Berggarten'.
4. 'G22088' has darker flowers than 'Berggarten'.
5. Plants of 'G22088' have been observed more tolerant to leaf pathogens (specifically powdery mildew) than the comparator 'Berggarten'.

Plants of the new cultivar 'G22088' are comparable to the unnamed, garden culinary *Salvia* commonly found in the horticulture market. The new cultivar 'G22088' differs in the following:

1. 'G22088' has larger, longer leaves than common culinary garden sage.
2. 'G22088' has thicker and broader leaves than common culinary garden sage.
3. 'G22088' has more rugose foliage than do common culinary garden sage.
4. 'G22088' has darker flowers than common culinary garden sage.
5. Leaves of 'G22088' are more intensely fragrant and flavorful than common culinary garden sage.

BRIEF DESCRIPTION OF THE PHOTOGRAPHS

Figure 2:
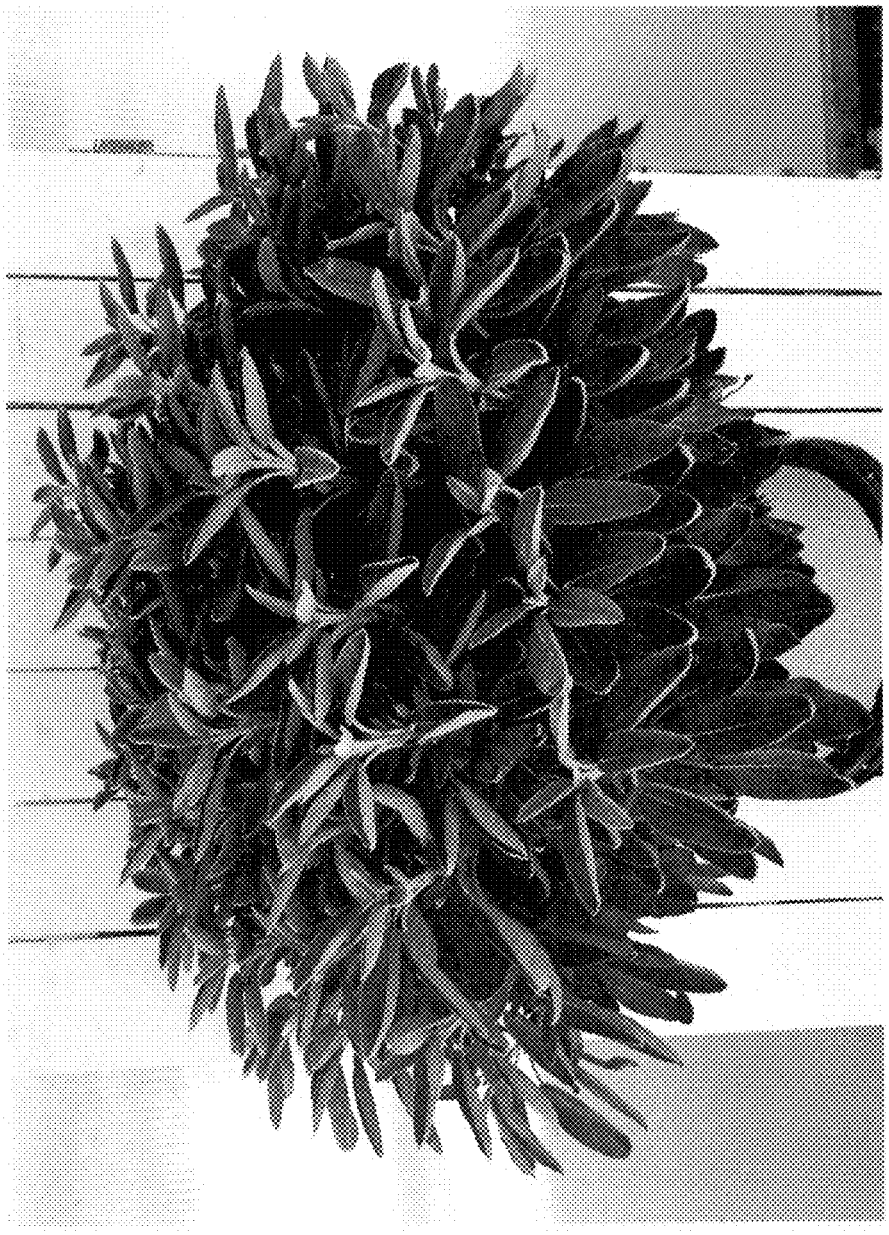

The accompanying photograph in FIG. 1 illustrates a typical flowering plant of 'G22088' grown outdoors in Columbus, OH at approximately 8-months old in the ground. FIG. 2 illustrates a non-flowering pot of the new variety at about 10 months old in a 12 inch pot. The photographs were taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart 2007 except where general terms of ordinary dictionary significance are used. The following observations and measurements describe 'G22088' plants grown outdoors in Camarillo, California. The growing temperature ranged from approximately 10° C. to 25° C. during the day and from approximately 6° C. to 12° C. during the night. General light conditions are normal sunlight and numerical values represent averages of typical plant types. Measurements were taken during June of 2024.

Botanical classification: *Salvia officianalis* 'G22088'.

Common Commercial Name: Culinary garden sage.

ROOTS

Root Description: Fine, densely fibrous. Colors include Green-White 157D on new growth and Orange-White 159C, Grey-Brown 199B and 199C for older roots.

PROPAGATION

Typical Method: Vegetative cuttings. Also true to type from tissue culture.

PLANT

Pot size of plant described: 1-gallon pot.

Height: Approximately 25 cm to top of foliage. Approximately 40 cm to top of flowering plane. Measured from soil level of pot.

Growth habit: Upright and upwardly spreading, forming a low mound.

Plant Spread: Approximately 45 cm.

Growth Rate: Rapid.

Branching Characteristics: Well-branched. Approximately 2 to 4 branches emerging from a pinch, which branch into another 2 to 4 primary lateral branches.

Length of Primary Lateral Branches: Approximately 12 cm.

Diameter of Primary Lateral Branches: Approximately 4 to 6 mm.

*Color*.—Near RHS Green 138A. Slight to no anthocyanin at nodes.

*Texture*.—Pubescent and ribbed.

Internode length: Average 2.5 cm.

Age of Plant Described: Approximately 20 weeks from 1 rooted cutting.

FOLIAGE

*Arrangement*.—Opposite.

*Quantity*.—Average range 6 to 12 fully expanded per main branch.

*Average Length*.—Approximately 6.5 cm. including petiole.

*Average Width*.—Approximately 2.6 cm.

*Shape of blade*.—Narrow ovate.

*Variegation*.—Absent.

*Apex*.—Acute.

*Base*.—Truncate.

*Attachment*.—Stalked.

*Margin*.—Very finely dentate.

*Texture of top surface*.—Matte, glabrous somewhat rugose.

*Texture of bottom surface*.—Matte, glabrous, reticulate to rugose.

*Color*.—Young foliage upper side: Near RHS Green 137D. Young foliage under side: Near RHS Green 137C. Mature foliage upper side: Near RHS Green 137B. Mature foliage under side: Near RHS Green 138B.

*Venation*.—Type: Reticulate. Venation color upper side: Near RHS Yellow-Green 145A. Venation color under side: Near RHS Yellow-Green 145C.

*Petiole*.—Average Length: Approximately 1.4 cm. Diameter: Approximately 3 mm Color: Near RHS Yellow-Green 145A.

*Fragrance*.—Strong sage scent.

FLOWER

Natural flowering season: Begins flowering in late Spring in California.

Inflorescence type and habit: Flowers arranged in verticillasters on spikes.

Flower Longevity on Plant: Individual flowers last approximately 7 to 10 days on the plant. Each spike lasts approximately 4 to 6 weeks with flowers. Corolla self cleaning, calyx persistent.

Quantity of flowers: About 12 to 16 fully opened flowers per spike, at one time. Mature plants have approximately 8 to 12 spikes.

Spike size:

*Diameter*.—Approximately 4.5 cm.

*Height*.—Approximately 8 to 11 cm.

*Inflorescence internode*.—8-11 mm.

*Number of florets per node*.—2 or 4 per node.

Individual Flowers:

Size:

*Diameter*.—Approximately 1.1 cm.

*Length*.—Approximately 2.5 cm.

*Fragrance*.—Sage scent, indistinguishable from foliage scent.

Corolla:

*Petal arrangement*.—The corolla is sympetalous and typically bilabiate with 2 small, fully fused lobes forming a single upper lip and 3 larger fused lobes forming a lower lip.

*Margin*.—Entire.

*Tip shape*.—Upper lip tip obtuse, lower lip tip retuse.

*Length*.—Upper lip Approximately 8 mm. Lower lip Approximately 5 mm Tube length Approximately 1.2 cm.

*Width*.—Upper lip: Approximately 6 mm, lower lip Approximately 5 mm. Tube width: Approximately 7 mm.

*Texture*.—Upper lip: Glabrous all surfaces. Lower lip: Glabrous all surfaces.

Color: Upper Lip:

*When opening*.—Inner surface: Near RHS Violet-Blue 90C Outer surface: Near RHS Violet-Blue 90B

*Fully opened*.—Inner surface: Near RHS Violet-Blue 90C Outer surface: Near RHS Violet-Blue 90C

*Fading*.—Inner surface: Near RHS Violet-Blue 91C Outer surface: Near RHS Violet-Blue 91C Color: Lower Lip:

*When opening*.—Inner surface: Near RHS Violet-Blue 90C Outer surface: Near RHS Violet-Blue 90B

*Fully opened*.—Inner surface: Near RHS Violet-Blue 90C Outer surface: Near RHS Violet-Blue 90C

*Fading*.—Inner surface: Near RHS Violet-Blue 91C Outer surface: Near RHS Violet-Blue 91C Color: Tube:

*When opening*.—Inner surface: Near RHS Violet 85D Outer surface: Near RHS Violet 85D

*Fully opened*.—Inner surface: Near RHS White N155C Outer surface: Near RHS Violet 85D Bud: Flower bud includes immature calyx which completely surrounds immature corolla.

*Shape*.—Ovoid.

*Length*.—Approximately 1.0 cm.

*Diameter*.—Approximately 7 mm.

*Color*.—Near RHS Violet-Blue 90B.

Calyx:

*Length*.—Approximately 1.5 cm.

*Diameter*.—Approximately 1.1 cm.

*Shape*.—Tubular, strongly flared distally.

Sepals:

*Shape*.—Quantity per flower: 3, fused to form a tube. Unfused apex.

*Length*.—Approximately 5 mm unfused portion.

*Width*.—Approximately 8 mm.

*Margin*.—Entire.

*Apex*.—Short apiculate.

*Texture*.—Softly pubescent.

*Color*.—Immature: Near RHS Green 138B flushed Purple N79B Mature: Near RHS Green 138B flushed Violet 83D Peduncle:

*Length*.—Average 4.0 cm.

*Diameter*.—5 mm. Color: RHS Green 138A

*Orientation*.—Straight, approximately 15-degree angle from center of plant.

*Strength*.—Strong.

*Texture*.—Softly pubescent, ridged.

Pedicels:

*Length*.—Average range 3 to 4 mm.

*Diameter*.—2 mm. Color: Near RHS Green 138B flushed Violet 83C

*Orientation*.—Straight, approximately 45 degree angle from attachment.

*Strength*.—Strong.

*Texture*.—Pubescent.

OTHER CHARACTERISTICS

Seeds: Very rarely produced. Small, black(203B) round seeds around 3 mm in diameter.

Disease/pest resistance: Observed tolerance to foliar diseases, specifically powdery mildew(*Golovinomyces* spp.) No increased resistance nor susceptibility to pests of *Salvia officianalis* observed.

Temperature range: USDA Zones 4-10.

What is claimed is:

1. A new and distinct cultivar of *Salvia* plant named 'G22088' as herein illustrated and described.

* * * * *